United States Patent [19]

Járai et al.

[11] 4,371,622

[45] Feb. 1, 1983

[54] MICROMONOSPORA CULTURE

[75] Inventors: Miklós Járai; Sándor Piukovich, both of Budapest; Sándor István, Szentendre; István Gado, Budapest; Valéria Széll, Budapest; István Barta, Budapest, all of Hungary

[73] Assignee: CHINOIN Gyogyszer es Vegyeszeti Termekek Gyara R.T., Budapest, Hungary

[21] Appl. No.: 116,916

[22] Filed: Jan. 30, 1980

[30] Foreign Application Priority Data

Jan. 2, 1979 [HU] Hungary .............................. CI 1906

[51] Int. Cl.³ .......................... C12N 1/20; C12R 1/29

[52] U.S. Cl. ...................................... 435/253; 435/867

[58] Field of Search .......................... 435/80, 253, 867

[56] References Cited

U.S. PATENT DOCUMENTS 3,832,286  8/1974  Weinstein et al. ..................... 435/80
3,956,068  5/1976  Weinstein et al. ..................... 435/80

*Primary Examiner*—Alvin E. Tanenholtz
*Attorney, Agent, or Firm*—Hubbell, Cohen, Stiefel & Gross

[57] ABSTRACT

*Micromonospora danubiensis*, a new species, having the capability of producing sisomicin.

2 Claims, No Drawings

MICROMONOSPORA CULTURE

This application relates to a new method for the production of sisomicin and the pharmaceutically acceptable salts thereof in a microbiological way.

Sisomicin / 0-2,6-diamino-2,3,4,6-tetradeoxyd-D-glyce-ro-hex-4-enopyranosyl-/-1→4/-0-(/3-deoxy-4-C-methyl-3-/methylamino)-β-L-arabopyranosyl-/1-6/)-2-desoxy-D-streptamine is an antibiotic with a wide spectrum.

Several methods of production of sisomicin by microbiologic methods are known. For example U.S. Pat. No. 3,832,286 and 3,907,771. According to these Patents the microorganism *Micromonospora inyoensis* (NRRL 3292) produces it as a main component.

The strain *Micromonospora grisea* (NRRL 3800) (U.S. Pat. No. 3,951,746), the *Micromonospora zionensis* (NRRL 5466) (U.S. Pat. No. 3,956,068), the *Micromonospora purpurea var. nigrescens* (MNG 00122) (Hungarian Pat. No. 168,778) are known to produce sisomicin.

In the course of investigating soil samples from the Danubian mud a new microorganism was isolated which produced sisomicin. This new microorganism was called JMS-1. The strain, which proved to be different from previously known microorganisms, was designated *Micromonospora danubiensis* species nova. From this microorganism we obtained, by different strain refining processes, the strain designated as JMS-3. During fermentation of this strain, which was deposited at the National Collection of Microorganisms, Budapest on the 19th of June 1978, there was a very high concentration of sisomicin in the fermentation medium.

This application describes a new method for the production of sisomicin which a strain of the microorganism *Micromonospora danubiensis*, ideally MNG 00171, is cultivated under aerobic conditions in a nutrient medium containing assimilable sources of carbon, nitrogen and mineral salts, and if required the resulting sisomicin will be isolated from the fermentation medium and purified and/or it will be transformed into a pharmaceutically acceptable salt.

The microorganism used in the method described in the application has the microscopic, macroscopic and biochemical properties set forth below.

MORPHOLOGY

Macroscopic observations: a 10 day old culture incubated at 37° C. on Czapek's agar shows a fair to moderate growth, no aerial mycelium, the colonies merge with a regular-round shape, and are light reddish-brown in color. No secretion of soluble pigments can be observed near the colonies.

Microscopic observations: Long, branched filaments without dividing wall, diameter of the filament 0.5μ, the spores are held by simple sporophones of 1-1.5μ diameter. The spores are oval-spherical shaped.

Biochemical and physiological properties: The strain *Micromonospora danubiensis* MNG-00171 grows moderately well at temperatures between 28° and 37° C., but no growth is observed at temperatures of 44° C. and above.

Utilization of the carbon source was studied with the following nutrient medium: Yeast extract 0.5%, carbon source 1.0%, $CaCO_3$ 0.1%, agar 1.5% in distilled water. Results are shown in Table 1:

TABLE 1

| Carbon source | *Micromonospora danubiensis* MNG 00171 |
|---|---|
| Arabinose | weak (−) |
| Ribose | moderate (+) |
| Xylose | weak (−) |
| Rhamnose | weak (−) |
| Fructose | fair (+ + +) |
| Galactose | moderate (+) |
| Glucose | fair (+ + +) |
| Lactose | weak (−) |
| Saccharose | fair (+ + +) |
| Raffinose | weak (−) |
| Dulcitol | weak (−) |
| Mannitol | fair (+ + +) |
| Inositol | weak (−) |
| Starch | fair (+ + +) |

Utilization of the nitrogen source was studied with the following nutrient medium: glucose 1%, agar 1.5% in distilled water. The results are shown in Table 2:

TABLE 2

| Nitrogen Source | *Micromonospora danubiensis* MNG 00171 |
|---|---|
| 0.5% Yeast extract | fair (+ + +) |
| 1% N—Z—Amine type A | fair (+ + +) |
| 1% Asparagine | moderate-weak (±) |
| 1% Glutamic acid | weak (−) |
| 1% $KNO_3$ | weak (−) |

A growing colony of *Micromonospora danubiensis* will hydrolyze gelatine, milk and starch and reduce nitrate to nitrite. The microorganism will tolerate a maximum of 2% sodium chloride in a growth medium.

CULTURAL CHARACTERISTICS

Table 3 sets forth culture characteristics of *Micromonospora danubiensis* JMS-3. (In describing the color formations for to the observations the following reference is employed: Baumenns Farbtonkarte Atla II., Paul Baumann, Aue I-SA 87350 LAu 302, GFR).

TABLE 3

| Medium | *Micromonospora danubiensis* MNG 00171 |
|---|---|
| Bennett agar | weak growth, vivid orange color Oc 97–98 |
| Czapek's agar | fair growth, reddish-brown color O 142–145 |
| Emerson's agar | no growth |
| Glucose-Asparagin agar | no growth |
| Glucose-Yeast-Extract Agar | fair growth, vivid orange color Oc 99 |
| Nutient agar | fair growth, wine-red some places yellow-brown color Ro 193, respectively Or 165–166 |
| Pepton Iron agar | no growth, or only in traces, small colonies, pale orange color, Oc 97 and CO 69, no diffusible pigment |
| Tyrosine agar | growth in traces, color cannot be determined, no diffusable pigment |
| Potato Plug without $CaCO_3$ | no growth |
| Potato Plug with $CaCO_3$ | moderate growth, reddish-brown color, O 136 and O 145–147 |

Based on the above mentioned facts it was ascertained that the Micromonospora strain designated as JMS-3 differs from the Micromonospora species discussed in literature. Comparison of the enlisted taxonomic marks with the Micromonospora system of Luedemann showed that the strain JMS-3 qualified as a new species, which due to its place of isolation was designated *Micromonospora danubiensis species nova*.

According to an advantageous realization the strain of *Micronomonspora danubiensis* is cultivated in submerged culture under aerobic conditions.

In the nutrient medium for the production of sisomicin, several carbon and nitrogen sources, assimilable by the microorganism *Micromonospora danubiensis*, inorganic salts, trace elements and antifoam additives can be present. As carbon, nitrogen and energy sources respectively, starch, soluble starch, dextrine, glucose, saccharose, corn meal, soya meal, hydrolysate of soya meal, hydrolysate of casein, corn steep liquor, yeast extract, etc. can be used.

As inorganic salts several ammonium, iron, zinc, manganese, magnesium, sodium, potassium and cobalt salts can be used. To enhance the buffer capacity of the nutrient medium advantageously calcium carbonate is used and as antifoam additive different vegetable oils (e.g. palm oil, sunflower oil, soya oil) can be used.

The use of different nutrient medium components allows production of different nutrient media. The food requirement for the production of the inoculum differs from that for the main fermentation. For the production of sisomicin one of the most beneficial nutrient media proved to be the nutrient medium containing soya meal, corn steep liquor, corn meal, starch, saccharose, calciumcarbonate, cobalt chloride and palm oil.

The temperature of fermentation may vary between 25° and 37° C. The fermentation is the most advantageous at a temperature of 28°-33° C.

Agitation depending on the geometry of the fermentor varies between 100 to 600 r.p.m. Advantageous aeration at about 1/1 v/v per minute.

The activity of the antibiotics produced in the course of fermentation (sisomicin and "minor" components) is determined by means of the test organism Staphylococcus epidermidis, with the agar-diffusion method, related to a standard sisomicin product.

During 96-120 hours of fermentation the sum of activity in the fermentation broth reaches a level of 400-450 U/ml (1 U=1 μg of sisomicin base activity). The sisomicin activity comes to about 85% of the total antibiotic activity in the fermentation broth.

The isolation of sisomicin may be carried out by known methods. If desired the sisomicin base obtained may be transformed into a pharmaceutically acceptable salt.

The quantity of sisomicin produced by the microorganism *Micromonospora danubiensis* is the multiple quantity of that produced up to the present by known methods. Under laboratory conditions it exceeds 450 U/ml and in the pilot plant fermentor 350-400 U/ml. The fermentation broth contains beside sisomicin only 10-15% of accompanying antibiotics.

The method according to the invention is illustrated by the following examples.

EXAMPLES 1. 100 ml of a sterile nutrient medium in a 500 ml Erlenmeyer flask of the following composition are inoculated under sterile conditions with 1 ml of a mycelium (vegetative germs $10^7$-$10^8$/ml) of the undercooled strain of *Micromonospora danubiensis* JMS-3 (MNG 00171):

| | |
|---|---|
| Starch | 25.0 g |
| Corn steep liquor | 7.0 g |
| $(NH_4)_2SO_4$ | 3.5 g |
| NaCl | 5.0 g |
| $CaCO_3$ | 8.0 g |
| Tap water | 1000 ml |

The pH value of the nutrient medium is adjusted to 7.5 before sterilization, thus after sterilization the pH value will be 7.0-7.2.

The culture is incubated for 3 days at 28° C. on a plane shaking machine (220 r.p.m., deviation 7.5 cm). With the culture thus obtained 6 liters of a sterile nutrient medium (in a glass fermentor of 10 liters) are inoculated under sterile conditions. The composition of the nutrient medium is the same as that of the inoculum nutrient medium set forth above.

The cultivation in the glass fermentor is carried out at 28° C., rotary agitation 400 r.p.m. and aeration 1/1 v/v per minute. As antifoam agent-as needed-palm oil is used.

The inoculum developed in 40 hours is applied for the inoculation of the fermentation nutrient medium. Quantity of the inoculum is 600 ml, quantity of the nutrient medium 6 liters, the pH value is 7.0-7.2 and volume of the fermentor 10 liters. Composition of the nutrient medium is the following:

| | |
|---|---|
| Soya meal | 50.0 g |
| Corn starch | 10.0 g |
| Saccharose | 30.0 g |
| $CaCO_3$ | 5.0 g |
| Corn steep liquor | 5.0 g |
| $CoCl_2.6H_2O$ | 4.5 mg |
| Tap water | 1000 ml |

Cultivation is carried out at 31° C., rotary agitation 400 r.p.m., aeration 6 liters/minute. As antifoam agent palm oil is used.

Production of the antibiotics starts in the 28-34$^{th}$ hour of fermentation and the highest value is achieved after 110 hours of fermentation.

At this time the total antibiotic content of the fermentation broth is determined to be 400 U/ml relative to a standard sisomicin using the test organism Staphylococcus epidermidis ad the agar diffusion method. (J. S. Simpson: Analytical Microbiology, Acad. Press, New York, p. 87-124, 1963).

2. The following nutrient medium is inoculated with the vegetative culture produced by the strain *Micromonospora danubiensis* JMS-3 (MNG 00171) on a plane shaking machine according to example 1:

| | |
|---|---|
| Soya meal | 10.0 g |
| Starch | 10.0 g |
| Saccharose | 10.0 g |
| $CaCO_3$ | 4.0 g |
| Tap water | 1000 ml |

The pH value of the nutrient medium after sterilization is 7.0-7.2, the quantity of the medium is 6 liters (in a 10 liter glass fermentor). The cultivation is carried out at 31° C., rotary agitation 400 r.p.m. and aeration 6 liters/minute. As antifoam agent-as needed-palm oil is used.

600 ml of the inoculum developed in 36 hours are used for inoculation of the fermentation nutrient medium of the following composition:

| Soya meal | 30.0 g |
|---|---|
| Corn meal | 25.0 g |
| CaCO$_3$ | 5.0 g |
| CoCl$_2$.6H$_2$O | 10.0 mg |
| Tap water | 1000 ml |

The pH value of the nutrient medium after sterilization is 7.0–7.2. Temperature of cultivation is 33° C., rotary agitation 600 r.p.m. and aeration 6 liters/minute. As antifoam agent palm oil is used.

Production of the antibiotics is started between the 26–30$^{th}$ hour of fermentation and the highest level is achieved after 100 hours of fermentation. At this moment the total antibiotic content of the fermentation broth is 420 U/ml relative to a standard sisomicin sample.

3. The following nutrient medium is inoculated with the vegetative culture produced by the strain *Micromonospora danubiensis* JMS-3 (MNG 00171) on a plane shaking machine according to the method of example 1:

| Starch | 25.0 g |
|---|---|
| Soya meal hydrolysate | 15.0 g |
| (NH$_4$)$_2$SO$_4$ | 2.0 g |
| NaCl | 3.0 g |
| ZnSO$_4$ | 0.5 g |
| CaCO$_3$ | 8.0 g |
| Tap water | 1000 ml |

The pH value of the nutrient medium after sterilization is 7.0–7.2, the quantity of the medium is 6 liters (in a 10 liter glass fermentor). The hydrolysis of the soya meal was carried out with NOVO bacterial protease at 60° C. for 30 minutes at a pH value of 7.5.

After inoculation the cultivation was carried out at 28° C., rotary agitation 400 r.p.m., aeration 6 liters/minute. As antifoam agent palm oil is used.

600 ml of the inoculum developed in 40 hours are used for the inoculation of the following fermentation nutrient medium:

| Soya meal hydrolysate | 50.0 g |
|---|---|
| Starch | 10.0 g |
| Dextrin | 25.0 g |
| CaCO$_3$ | 5.0 g |
| Saccharose | 10.0 g |
| CoCl$_2$.6H$_2$O | 4.5 mg |
| Tap water | 1000 ml |

The pH value of the nutrient medium after sterilization is 7.0–7.2, the quantity of the medium is 6 liters (in a 10 liter glass fermentor). The hydrolysis of the soya meal was carried out with NOVO bacerial protease at 60° C. for 30 minutes at a pH value of 7.5.

After inoculation the cultivation was carried out at 31° C., rotary agitation 600 r.p.m., aeration 6 liters/minute. As antifoam agent palm oil was used.

Production of the antibiotics is started between the 26–30$^{th}$ hour of fermentation, the highest value is achieved after 100 hours of fermentation. At this time the total antibiotica content of the fermentation broth is 430 U/ml relative to a standard sisomicin sample.

4. The following nutrient medium, a quantity of 200 liters (volume of the forefermentor built of stainless steel is 300 liters) is inoculated with the vegetative culture produced by the strain *Micromonospora danubiensis* JMS-3 (MNG 00171) in a glass fermentor according to example 2:

| Soya meal | 10.0 g |
|---|---|
| Starch | 10.0 g |
| Saccharose | 10.0 g |
| CaCO$_3$ | 4.0 g |
| Tap water | 1000 ml |

The pH value of the nutrient medium after sterilization is 7.0–7.2. As antifoam agent palm oil is used.

Cultivation is carried out at 31° C., rotary agitation 180 r.p.m., aeration 200 liters/minute.

The inoculum developed in 36 hours is used for the inoculation of the fermentation nutrient medium of the following composition (the volume of the medium is 2000 l):

| Soya meal | 30.0 g |
|---|---|
| Corn meal | 25.0 g |
| CaCO$_3$ | 5.0 g |
| CoCl$_2$.6H$_2$O | 10.0 mg |
| Tap water | 1000 ml |

The pH value of the nutrient medium after sterilization is 7.0–7.2. Temperature of cultivation is 33° C., rotary agitation 220 r.p.m., aeration 2 m$^3$/minute, as antifoam agent a mixture of soya oil and palm oil (50%–50%) is used.

Production of the antibiotics is started between the 26–30$^{th}$ hours of fermentation and the highest level is achieved after 100 hours of fermentation. At this time the total antibiotic content of the fermentation broth is 380 U/ml relative to a standard sisomicin sample.

The fermentation finished, proceeding by known methods 288 g of a pure sisomicin base are obtained, which also contains bound water.

Characteristics of the product:

Melting point: 198–201° C.

[α]D = +188° (c = 0.3 water)

Elementary analysis:

calculated on monohydrate: C = 49.80%, H = 8.2%, N = 14.95%;

found: C = 49.15%, H = 8.37%, N = 15.15%

IR-spectrum (KBr): $\nu$OH, NH 3170–3360, $\nu$CH=COC 1690, $\nu$COC 1060 cm$^{-1}$.

PMR-spectrum (D$_2$ 0): δ1.20 (Me-4″,s, 3H), δ2.50 (Me-N-3″,s, 3H), δ2.56 (H-3″, d, J$_{2',3'}$ = 10 Hz, 1H), δ3.17 (H-6′, bs, 2H), δ3.30 (H$_{ax}$-5″, d, J$_{gem}$ = = 12 Hz, 1H), δ3.80 (H-2″, dd, J$_{2''},$ $_{3''}$ = = 10 Hz, J$_{1'',2''}$ = 4 Hz, 1H), δ4.04 (H$_{e}$-5″, d, J$_{gem}$ = 12 Hz, 1H), δ4.88 (H-4′, bt, 1H), δ5.09 (H-1 ″, d, J$_{1'',\ 2''}$ = 4 Hz, 1H), δ5.35 (H-1′, d, J$_{1',\ 2'}$ = 2 Hz, 1H) ppm.

Mass numbers of the characteristic ions (m/e): 477, 332, 304, 160, 145, 127, 118, 110, 100.

PREPARATION OF SISOMICIN SULFATE 15 g of the pure sisomicin base are dissolved in 60 ml of ion free water and to that solution as much 5 N sulfuric acid solution is added dropwise, as in needed to obtain a level of pH 4.3. Thereafter 1.5 g of active charcoal are added to the solution and the mixture is stirred for 30 minutes, then filtered on Seitz sheet. The filter is washed with 3×50 ml of ion free water and the unified filtrate is added by continuous stirring to 1 liter of methanol. The solution containing separated precipitate is allowed to stand in a cooling room, whereafter the precipitate is filtered out. The filtered sisomicin sulfate is washed with 3×50 ml of methanol, and dried in vacuum at 50° C. above $P_2O_5$ to constant weight. Thus 22 g of sisomicin sulfate are obtained.

We claim:

1. A substantially biologically pure culture of the actinomyces species *Micromonospora danubiensis* having the capability of producing sisomicin upon cultivation in an aqueous nutrient medium.

2. A substantially biologically pure culture of the actinomyces strain *Micromonospora danubiensis* MNG-00171 having the capability of producing sisomicin upon cultivation in an aqueous nutrient medium.

* * * * *